US012338194B2

(12) United States Patent
Dewilde et al.

(10) Patent No.: US 12,338,194 B2
(45) Date of Patent: Jun. 24, 2025

(54) PROCESSES FOR EFFICIENT AND SUSTAINED PRODUCTION OF C2 TO C4 OLEFINS

(71) Applicant: Dow Global Technologies LLC, Midland, MI (US)

(72) Inventors: Joseph F. Dewilde, Midland, MI (US); Adam Chojecki, Ghent (BE); Alexey Kirilin, Terneuzen (NL); Ewa A. Tocha-Bielak, Terneuzen (NL); David F. Yancey, Midland, MI (US); Glenn Pollefeyt, Wondelgem (BE); Davy L.S. Nieskens, Terneuzen (NL); Andrzej Malek, Midland, MI (US)

(73) Assignee: Dow Global Technologies LLC, Midland, MI (US)

( * ) Notice: Subject to any disclaimer, the term of this patent is extended or adjusted under 35 U.S.C. 154(b) by 586 days.

(21) Appl. No.: 17/785,740

(22) PCT Filed: Dec. 14, 2020

(86) PCT No.: PCT/US2020/064826
§ 371 (c)(1),
(2) Date: Jun. 15, 2022

(87) PCT Pub. No.: WO2021/126752
PCT Pub. Date: Jun. 24, 2021

(65) Prior Publication Data
US 2023/0062065 A1    Mar. 2, 2023

Related U.S. Application Data

(60) Provisional application No. 62/950,548, filed on Dec. 19, 2019.

(51) Int. Cl.
| | | |
|---|---|---|
| *C07C 1/04* | (2006.01) | |
| *B01J 21/06* | (2006.01) | |
| *B01J 23/10* | (2006.01) | |
| *B01J 29/85* | (2006.01) | |
| *B01J 35/30* | (2024.01) | |
| *B01J 35/61* | (2024.01) | |

(52) U.S. Cl.
CPC ............ *C07C 1/043* (2013.01); *B01J 21/066* (2013.01); *B01J 23/10* (2013.01); *B01J 29/85* (2013.01); *B01J 35/391* (2024.01); *B01J 35/613* (2024.01); *C07C 2521/06* (2013.01); *C07C 2523/08* (2013.01); *C07C 2523/10* (2013.01); *C07C 2529/85* (2013.01)

(58) Field of Classification Search
CPC . C07C 1/043; C07C 2521/06; C07C 2523/08; C07C 2523/10; C07C 2529/85; C07C 11/04; C07C 11/06; C07C 11/08; B01J 21/066; B01J 23/10; B01J 29/85; B01J 35/391; B01J 29/7015
See application file for complete search history.

(56) References Cited

U.S. PATENT DOCUMENTS

| | | | |
|---|---|---|---|
| 9,919,981 B2 | 3/2018 | Chojecki et al. | |
| 2016/0102033 A1 | 4/2016 | Yang et al. | |

FOREIGN PATENT DOCUMENTS

| | | |
|---|---|---|
| CN | 110180549 A | 8/2019 |
| CN | 110227539 A | 9/2019 |
| WO | 2017/074558 A1 | 5/2017 |
| WO | 2018119194 A1 | 6/2018 |
| WO | 2018119195 A1 | 6/2018 |

OTHER PUBLICATIONS

Argentine Office Action dated May 29, 2024, pertaining to AR Patent Application No. 2020 01 03268, 2 pgs.
Nieskens, Davy L. S., et al., "Understanding the Enhanced Lifetime of SAPO-34 in a Direct Syngas-to-Hydrocarbons Process", ACS Catalysis, vol. 9, pp. 691-700 (2019).
Communication pursuant to Rules 161(1) and 162 EPC, dated Jul. 26, 2022, pertaining to EP Patent Application No. 20838832.2 3 pages.
International Preliminary Report on Patentability, dated Jun. 30, 2022, pertaining to International Patent Application No. PCT/US2020/064826 8 pages.
Kuwait Examination Report dated Aug. 5, 2024, pertaining to KW Patent Application No. KW/P/2022/000752, 5 pgs.
Brazilian Technical Report dated Nov. 26, 2024, pertaining to BR Patent Application No. BR 112022011041-3, 9 pgs.
Jiao, Feng, et al., "Selective conversion of syngas to light olefins," Science, vol. 351, Issue 6277, pp. 1065-1068 (Downloaded Mar. 4, 2016).
Arora, Sukaran S., et al., "Lifetime improvement in methanol-to-olefins catalysis over chabazite materials by high-pressure H2 co-feeds," Nature Catalysis, vol. 1, pp. 666-672 (Sep. 2018).
Cheng, Kang, et al., "Direct and Highly Selective Conversion of Synthesis Gas into Lower Olefins: Design of a Bifunctional Catalyst Combining Methanol Synthesis and Carbon-Carbon Coupling," Angewandte Chemie International Edition, vol. 55, No. 15, pp. 4725-4728 (Mar. 9, 2016).
International Search Report and Written Opinion received from the European Patent Office acting as International Searching Authority for International Patent Application PCT/US2020/064826 dated Mar. 17, 2021 (14 total pages).
Chinese Office Action and Search Report, dated Jul. 22, 2023, pertaining to Chinese Patent Application No. 202080084346.8, 8 pgs.

*Primary Examiner* — Jafar F Parsa
(74) *Attorney, Agent, or Firm* — Dinsmore & Shohl LLP (57) ABSTRACT

A process for preparing $C_2$ to $C_4$ olefins includes introducing a feed stream of hydrogen gas and a carbon-containing gas into a reaction zone of a reactor and converting the feed stream into a product stream including $C_2$ to $C_4$ olefins in the reaction zone in the presence of a hybrid catalyst and in a non-oxidative atmosphere. The hybrid catalyst includes a metal oxide catalyst component comprising gallium oxide and zirconia, and a microporous catalyst component having an 8 membered ring structure. The process also includes periodically introducing an oxidative atmosphere into the reaction zone.

18 Claims, 6 Drawing Sheets

PROCESSES FOR EFFICIENT AND SUSTAINED PRODUCTION OF C2 TO C4 OLEFINS

CROSS REFERENCE TO RELATED APPLICATIONS

This application claims priority to U.S. Provisional Patent Application No. 62/950,548, filed on Dec. 19, 2019, the entire disclosure of which is hereby incorporated by reference.

BACKGROUND

Field

The present specification generally relates to processes that efficiently convert various carbon-containing streams to $C_2$ to $C_4$ olefins. In particular, the present specification relates to process methods that achieve sustained conversion of synthesis gas feeds resulting in good conversion of carbon and high yield of desired products. The synthesis gas comprises hydrogen gas and a carbon-containing gas selected from the group consisting of carbon monoxide, carbon dioxide, and mixtures thereof. A hybrid catalyst generally comprises a combination of a metal oxide component and a microporous catalyst component that operate in tandem.

Technical Background

For a number of industrial applications, olefins are used, or are starting materials used, to produce plastics, fuels, and various downstream chemicals. Such olefins include $C_2$ to $C_4$ materials, such as ethylene, propylene, and butylenes (also commonly referred to as ethene, propene and butene, respectively). A variety of processes for producing these lower olefins have been developed, including petroleum cracking and various synthetic processes.

Synthetic processes for converting feed carbon to desired products, such as olefins, are known. Some of these synthetic processes use a hybrid catalyst. Different types of catalysts have also been explored, as well as different kinds of feed streams and proportions of feed stream components. However, many of these synthetic processes have low carbon conversion and much of the feed carbon either (1) does not get converted and exits the process in the same form as the feed carbon; (2) is converted to $CO_2$; or (3) these synthetic processes have low stability over time and the catalyst loses its activity for carbon conversion to desirable products. For example, many synthetic processes tend to have decreased $C_2$ to $C_4$ olefin production over time.

Accordingly, a need exists for processes that have a high conversion of feed carbon to desired products, such as, for example, $C_2$ to $C_4$ olefins, in combination with a high on-stream stability of the catalyst.

SUMMARY

According to one embodiment, a process for preparing $C_2$ to $C_4$ olefins comprises: introducing a feed stream comprising hydrogen gas and a carbon-containing gas selected from the group consisting of carbon monoxide, carbon dioxide, and mixtures thereof into a reaction zone of a reactor; converting the feed stream into a product stream comprising $C_2$ to $C_4$ olefins in the reaction zone in the presence of a hybrid catalyst and in a non-oxidative atmosphere, the hybrid catalyst comprising: a metal oxide catalyst component comprising gallium oxide and zirconia; and a microporous catalyst component comprising an 8 membered ring pore opening; and periodically introducing an oxidative atmosphere into the reaction zone.

Additional features and advantages will be set forth in the detailed description which follows, and in part will be readily apparent to those skilled in the art from that description or recognized by practicing the embodiments described herein, including the detailed description which follows and the claims.

It is to be understood that both the foregoing general description and the following detailed description describe various embodiments and are intended to provide an overview or framework for understanding the nature and character of the claimed subject matter.

DETAILED DESCRIPTION

Reference will now be made in detail to embodiments of processes using the hybrid catalyst to prepare $C_2$ to $C_4$ olefins.

The use of hybrid catalysts to convert feed streams comprising carbon to desired products, such as, for example, $C_2$ to $C_4$ olefins, is known. However, many known hybrid catalysts are inefficient, because they exhibit decreased $C_2$ to $C_4$ olefin selectivity as time on stream increases. One way that this decreased $C_2$ to $C_4$ olefin selectivity is observed is by an increase in selectivity of other components, such as, for example, by having an increase in methane production (selectivity) and/or an increase in paraffin productivity as time on stream increases, which results in decreasing olefin yield under a given set of operating conditions over a given period of time. In contrast, processes for forming $C_2$ to $C_4$ olefins disclosed and described herein exhibit a high and steady yield of $C_2$ to $C_4$ olefins, even as the catalyst time on stream increases. The processes and hybrid catalysts used in the processes according to embodiments are discussed below.

As a summary, hybrid catalysts closely couple independent reactions on each of the two independent catalysts. In the first step, a feed stream comprising hydrogen gas ($H_2$) and at least one of carbon monoxide (CO), carbon dioxide ($CO_2$), or a mixture of CO and $CO_2$, such as, for example, syngas, is converted into an intermediate(s) such as oxygenated hydrocarbons. In the subsequent step, these intermediates are converted into hydrocarbons (mostly short chain hydrocarbons, such as, for example $C_2$ to $C_4$ olefins). The continued formation and consumption of the intermediate oxygenates formed in the first step by the reactions of the second step ensures that there is no thermodynamic limit on conversions of the feed. With a careful selection of the components to the hybrid catalytic bed, high conversions of the syngas feed can be achieved.

Hybrid catalyst systems comprise a metal oxide catalyst component, which converts the feed stream to oxygenated hydrocarbons, and a microporous catalyst component (such as, for example, a silicoaluminophosphate or SAPO-type molecular sieve component), which converts the oxygenated hydrocarbons to hydrocarbons. Known hybrid catalyst systems generally exhibit a trade-off between initial yield of $C_2$ to $C_4$ olefins and sustained yield of $C_2$ to $C_4$ olefins as the catalyst time on stream increases (also referred to as stability). There is accordingly a need for methods that result in a high initial yield as well as a high stability when used with a hybrid catalyst.

Embodiments of hybrid catalysts used in processes disclosed herein comprise a metal oxide catalyst component comprising: (1) gallium oxide ($Ga_2O_3$), and (2) zirconia ($ZrO_2$). In some embodiments, the zirconia may be crystalline, and in some embodiments, the zirconia may be monoclinic crystalline phase pure zirconia. The metal oxide catalyst component is combined with a microporous catalyst component. The microporous catalyst component is, according to some embodiments, an microporous catalyst component comprising an 8 membered ring pore opening, such as, for example, SAPO-34 molecular sieve.

In embodiments disclosed herein, the composition of the metal oxide catalyst component is designated by a weight percentage of the gallium metal to the zirconia. In one or more embodiments, the composition of the metal oxide catalyst component is designated by weight of gallium per 100 grams (g) of zirconia. According to embodiments, the metal oxide catalyst component comprises from greater than 0.0 g gallium to 30.0 g gallium per 100 g of zirconia, such as 5.0 g gallium to 30.0 g gallium per 100 g of zirconia, 10.0 g gallium to 30.0 g gallium per 100 g of zirconia, 15.0 g gallium to 30.0 g gallium per 100 g of zirconia, 20.0 g gallium to 30.0 g gallium per 100 g of zirconia, or 25.0 g gallium to 30.0 g gallium per 100 g of zirconia. In some embodiments, the metal oxide catalyst component comprises from greater than 0.0 g gallium to 25.0 g gallium per 100 g of zirconia, such as from greater than 0.0 g gallium to 20.0 g gallium per 100 g of zirconia, from greater than 0.0 g gallium to 15.0 g gallium per 100 g of zirconia, from greater than 0.0 g gallium to 10.0 g gallium per 100 g of zirconia, or from greater than 0.0 g gallium to 5.0 g gallium per 100 g of zirconia.

Although gallium oxide and zirconia metal oxide catalyst components are described above, it should be understood that other metal oxide catalyst components can be used in embodiments disclosed and described herein. It should also be understood that according to embodiments, the metal oxide catalyst component may be made by methods that lead to intimate contact between the gallium and zirconia.

In one or more embodiments, after the metal oxide catalyst component has been formed the metal oxide catalyst component is physically mixed with a microporous catalyst component. The microporous catalyst component is, in embodiments, selected from molecular sieves having 8-MR pore openings and having a framework type selected from the group consisting of the following framework types CHA, AEI, AFX, ERI, LEV, LTA, UFI, RTH, EDI, GIS, MER, RHO, and combinations thereof, the framework types corresponding to the naming convention of the International Zeolite Association (IZA). It should be understood that in embodiments, both aluminosilicate and silicoaluminophosphate frameworks may be used. Some embodiments may include tetrahedral aluminosilicates, ALPOs (such as, for example, tetrahedral aluminophosphates), SAPOs (such as, for example, tetrahedral silicoaluminophosphates), and silica-only based tectosilicates. In certain embodiments, the microporous catalyst component may be silicoaluminophosphate having a Chabazite (CHA) framework type. Examples of these may include, but are not necessarily limited to: CHA embodiments selected from SAPO-34 and SSZ-13; and AEI embodiments such as SAPO-18. Combinations of microporous catalyst components having any of the above framework types may also be employed. It should be understood that the microporous catalyst component may have different membered ring pore opening depending on the desired product. For instance, microporous catalyst component having 8-MR to 12-MR pore openings could be used depending on the desired product. However, to produce $C_2$ to $C_4$ olefins, a microporous catalyst component having 8-MR pore openings is used in embodiments.

The metal oxide catalyst component and the microporous catalyst component of the hybrid catalyst may be mixed together by any suitable means, such as, for example, by physical mixing—such as shaking, stirring, or other agitation. The metal oxide catalyst component may, in embodiments, comprise from 5.0 wt % to 95.0 wt % of the hybrid catalyst, such as from 10.0 wt % to 90.0 wt %, from 15.0 wt % to 85.0 wt %, from 20.0 wt % to 80.0 wt %, from 25.0 wt % to 75.0 wt %, from 30.0 wt % to 70.0 wt %, from 35.0 wt % to 65.0 wt %, from 40.0 wt % to 60.0 wt %, or from 45.0 wt % to 55.0 wt %.

After the metal oxide catalyst component has been formed and combined with a microporous catalyst component to form a hybrid catalyst, the hybrid catalyst may be used in processes for converting carbon in a carbon-containing feed stream to $C_2$ to $C_4$ olefins. The processes disclosed and described herein may provide improved $C_2$ to $C_4$ olefin selectivity by the hybrid catalyst as time on stream increases when compared to conventional systems. In particular, and without being bound by any particular theory, it is believed that periodically exposing the hybrid catalyst to oxidative atmosphere can lead to higher stability of $C_2$ to $C_4$ olefin yield over time. As used herein, "periodic," "periodically," "period," and similar terms describe a process where an oxidative atmosphere is applied to the hybrid catalyst bed in an alternative manner to syngas feed. It should be understood that in embodiments, the frequency at which the periods occur may be uniform (such as, for example occurring every 100 hours the hybrid catalyst is on stream), but in one or more embodiments the frequency at which the periods occur may not be uniform (such as, for example, occurring at 100 hours on stream, 175 hours on stream, 225 hours on stream). Processes according to embodiments disclosed and described herein will be provided in more detail below.

According to embodiments, a feed stream is fed into a reaction zone, the feed stream comprises hydrogen ($H_2$) gas and a carbon-containing gas selected from carbon monoxide (CO), carbon dioxide ($CO_2$), and combinations thereof. In some embodiments, the $H_2$ gas is present in the feed stream in an amount of from 10 volume percent (vol %) to 90 vol %, based on combined volumes of the $H_2$ gas and the gas selected from CO, $CO_2$, and combinations thereof. The feed stream is contacted with a hybrid catalyst as disclosed and described herein in the reaction zone. The hybrid catalyst comprises a metal oxide catalyst component comprising gallium oxide and zirconia, and comprises a microporous catalyst component, which in embodiments may have an 8-MR pore openings, such as, for example, SAPO-34.

It should be understood that the apparent activity referenced as a percentage of converted carbon oxides of the hybrid catalyst may vary with the varied concentration of hydrogen and carbon oxides in the feed. For example, for feed streams containing CO as the carbon-containing gas the apparent activity can be higher and that the apparent activity of the hybrid catalyst decreases as a larger portion of the carbon-containing gas in the feed stream is $CO_2$. However, that is not to say that the hybrid catalyst disclosed and described herein cannot be used in methods where the feed stream comprises $CO_2$ as all, or a large portion, of the carbon-containing gas.

The feed stream is contacted with the hybrid catalyst in the reaction zone under reaction conditions sufficient to form a product stream comprising $C_2$ to $C_4$ olefins. The reaction conditions comprise a temperature within the reaction zone ranging, according to one or more embodiments, from 300° C. to 500° C., such as from 300° C. to 475° C., from 300° C. to 450° C., from 300° C. to 425° C., from 300° C. to 400° C., from 300° C. to 375° C., from 300° C. to 350° C., or from 300° C. to 325° C. In other embodiments, the temperature within the reaction zone is from 325° C. to 500° C., from 350° C. to 500° C., from 375° C. to 500° C., from 400° C. to 500° C., from 425° C. to 500° C., from 450° C. to 500° C., or from 475° C. to 500° C. In yet other embodiments, the temperature within the reaction zone is from 300° C. to 500° C., such as from 325° C. to 475° C., from 350° C. to 450° C., or from 360° C. to 440° C.

The reaction conditions also, in embodiments, include a pressure inside the reaction zone of at least 1 bar (100 kilopascals (kPa), such as at least 5 bar (500 kPa), at least 10 bar (1,000 kPa), at least 15 bar (1,500 kPa), at least 20 bar (2,000 kPa), at least 25 bar (2,500 kPa), at least 30 bar (3,000 kPa), at least 35 bar (3,500 kPa), at least 40 bar (4,000 kPa), at least 45 bar (4,500 kPa), at least 50 bar (5,000 kPa), at least 55 bar (5,500 kPa), or at least 60 bar (6,500 kPa). In other embodiments, the reaction conditions include a pressure inside the reaction zone that is from 5 bar (500 kPa) to 70 bar (7,000 kPa), such as from 10 bar (1,000 kPa) to 60 bar (6,000 kPa), from 15 bar (1,500 kPa) to 50 bar (5,000 kPa), from 20 bar (2,000 kPa) to 35 bar (3,500 kPa), or from 25 bar (2,500 kPa) to 30 bar (3,000 kPa). In one or more embodiments, the pressure inside the reaction zone is from 30 bar (3,000 kPa) to 40 bar (4,000 kPa), such as from 31 bar (3,100 kPa) to 39 bar (3,900 kPa), from 32 bar (3,200 kPa) to 38 bar (3,800 kPa), from 33 bar (3,300 kPa) to 37 bar (3,700 kPa), or from 34 bar (3,400 kPa) to 36 bar (3,600 kPa). In an embodiment, the pressure inside the reaction zone is from 40 bar (4,000 kPa) to 50 bar (5,000 kPa), such as from 42 bar (4,200 kPa) to 48 bar (4,800 kPa), or from 44 bar (4,400 kPa) to 46 bar (4,600 kPa).

According to embodiments, the gas hour space velocity (GHSV) within the reaction zone is from 1,200 per hour (/h) to 12,000/h, such as from 1,500/h to 10,000/h, from 2,000/h to 9,500/h, from 2,500/h to 9,000/h, from 3,000/h to 8,500/h, from 3,500/h to 8,000/h, from 4,000/h to 7,500/h, from 4,500/h to 7,000/h, from 5,000/h to 6,500/h, or from 5,500/h to 6,000/h. In some embodiments the GHSV within the reaction zone is from 1,800/h to 3,600/h, such as from 2,000/h to 3,600/h, from 2,200/h to 3,600/h, from 2,400/h to 3,600/h, from 2,600/h to 3,600/h, from 2,800/h to 3,600/h, from 3,000/h to 3,600/h, from 3,200/h to 3,600/h, or from 3,400/h to 3,600/h. In some embodiments, the GHSV within the reaction zone is from 1,800/h to 3,400/h, such as from 1,800/h to 3,200/h, from 1,800/h to 3,000/h, from 1,800/h to 2,800/h, from 1,800/h to 2,600/h, from 1,800/h to 2,400/h, from 1,800/h to 2,200/h, or from 1,800/h to 2,000/h. In some embodiments, the GHSV within the reaction is from 2,000/h to 3,400/h, such as from 2,200/h to 3,200/h, from 2,400/h to 3,000/h, or from 2,600/h to 2,800/h.

The above conditions are used to convert a feed stream comprising $H_2$ gas and a carbon-containing gas selected from CO, $CO_2$, and combinations thereof to a product stream that comprises a significant amount of $C_2$ to $C_4$ olefins. These conditions are also referred to hereinafter as "conversion conditions." However, it has been found that as the time on stream of the hybrid catalyst increases, the $C_2$ to $C_4$ olefin selectivity decreases, and the methane ($CH_4$) and/or $C_2$ to $C_4$ paraffins (such as ethane, propane, and butane) selectivity increases. In processes where $C_2$ to $C_4$ olefins are the target product, this decrease in $C_2$ to $C_4$ olefin selectivity as time on stream increases is not desirable as it decreases the production of desirable products, negatively impacts process economics, and can lead to down time of the system and increased costs to replace the hybrid catalyst. However, without being bound by any particular theory, it has been found that periodically introducing an oxidative atmosphere into the reaction zone to expose the hybrid catalyst to the oxidative atmosphere exhibits a high and steady yield of $C_2$ to $C_4$ olefins, even as the catalyst time on stream increases.

The periodic exposure of the hybrid catalyst to an oxidative atmosphere does not increase the activity of the hybrid catalyst. This is different from conventional regeneration processes, which generally refer a treatment that renews the rate at which the hybrid catalyst converts carbon in the feed stream (such as, for example, CO or $CO_2$) to any hydrocarbons (such as, for example, olefins and/or paraffins). This carbon conversion is generally referred to as "activity" or "carbon conversion." As an example, a process may have a very high activity where 90% of the carbon in the feed stream is converted to paraffins, but the process may not produce any olefins. In this example, the activity (or conversion) of the hybrid catalyst is 90%, but the $C_2$ to $C_4$ olefin selectivity is 0%. Likewise, the activity of a hybrid catalyst may remain relatively constant as time on stream increases, but the $C_2$ to $C_4$ olefin selectivity may decrease as time on stream increases. For example, the activity of the hybrid catalyst may only drop from 90% to 80% after 500 hours on stream, but the $C_2$ to $C_4$ olefin selectivity may decrease from 40% at 5 hours on stream to 5% at 500 hours on stream. Regeneration would be conducted to return the activity of the hybrid catalyst to 90%.

The processes disclosed and described herein differ from typical regeneration processes because they do not address the activity of the hybrid catalyst as time on stream increases. Rather, the processes disclosed and described herein exhibit a high and steady yield of $C_2$ to $C_4$ olefins, even as the catalyst time on stream increases. For example, by using processes according to embodiments disclosed and described herein, the $C_2$ to $C_4$ olefin selectivity may only decrease from 40% at 5 hours on stream to 35% at 500 hours on stream. Thus, processes according to embodiments disclosed and described exhibit a high and steady yield of $C_2$ to $C_4$ olefins, even as the catalyst time on stream increases.

As noted above, a feed stream used in processes of embodiments comprises $H_2$ gas and a carbon-containing gas selected from CO, $CO_2$, and combinations thereof. Accordingly, the initial atmosphere—and the atmosphere present during the conversion conditions—within the reaction zone is generally $H_2$ gas and a carbon-containing gas selected from CO, $CO_2$, and combinations thereof. Namely, the atmosphere within the reaction zone during the conversion conditions where carbon gas (such as CO or $CO_2$) is converted to hydrocarbons is a non-oxidative atmosphere. As used herein, a non-oxidative atmosphere is an atmosphere that does not comprise enough oxygen so that oxidation or other oxidizing reactions can occur. In embodiments, the non-oxidative atmosphere comprises less than 0.10 vol % oxygen, such as less than 0.05 vol % oxygen, or less than 0.02 vol % oxygen. Because Hz, and CO are reductive gases, little to no oxidation occurs while the process is conducted under normal operating conditions, which were previously described. Under these normal operating conditions, the $C_2$ to $C_4$ olefin selectivity of the hybrid catalyst will decrease as time on stream increases. In processes, the $C_2$ to $C_4$ olefin selectivity of the hybrid catalyst can decrease by 50% or more after 1000 hours on stream. However, as described above, this decrease in $C_2$ to $C_4$ olefin selectivity as time on stream increases may be substantially avoided by periodically introducing an oxidative atmosphere into the reaction zone.

The concentration of oxygen in the oxidative atmosphere that is periodically introduced into the reaction zone is not particularly limited. For example, the oxygen concentration in the oxidative atmosphere may be from 0.1 volume percent (vol %) to 99.9 vol %, such as from 5.0 vol % to 95.0 vol %, from 10.0 vol % to 90.0 vol %, from 15.0 vol % to 85.0 vol %, from 20.0 vol % to 80.0 vol %, from 25.0 vol % to 75.0 vol %, from 30.0 vol % to 70.0 vol %, from 35.0 vol % to 65.0 vol %, from 40.0 vol % to 60.0 vol %, or from 45.0 vol % to 55.0 vol %. In one or more embodiments, the concentration of oxygen in the oxidative atmosphere that is periodically introduced in the reaction zone is relatively low, such as from 0.1 vol % to 5.0 vol %, from 0.2 vol % to 5.0 vol %, from 0.5 vol % to 5.0 vol %, from 0.8 vol % to 5.0 vol %, from 1.0 vol % to 5.0 vol %, from 1.2 vol % to 5.0 vol %, from 1.5 vol % to 5.0 vol %, from 1.8 vol % to 5.0 vol %, from 2.0 vol % to 5.0 vol %, from 2.2 vol % to 5.0 vol %, from 2.5 vol % to 5.0 vol %, from 2.8 vol % to 5.0 vol %, from 3.0 vol % to 5.0 vol %, from 3.2 vol % to 5.0 vol %, from 3.5 vol % to 5.0 vol %, from 3.8 vol % to 5.0 vol %, from 4.0 vol % to 5.0 vol %, from 4.2 vol % to 5.0 vol %, from 4.5 vol % to 5.0 vol %, or from 4.8 vol % to 5.0 vol %. In embodiments, the concentration of oxygen in the oxidative atmosphere that is periodically introduced in the reaction zone is from 0.1 vol % to 4.8 vol %, such as from 0.1 vol % to 4.5 vol %, from 0.1 vol % to 4.2 vol %, from 0.1 vol % to 4.0 vol %, from 0.1 vol % to 3.8 vol %, from 0.1 vol % to 3.5 vol %, from 0.1 vol % to 3.2 vol %, from 0.1 vol % to 3.0 vol %, from 0.1 vol % to 2.8 vol %, from 0.1 vol % to 2.5 vol %, from 0.1 vol % to 2.2 vol %, from 0.1 vol % to 2.0 vol %, from 0.1 vol % to 1.8 vol %, from 0.1 vol % to 1.5 vol %, from 0.1 vol % to 1.2 vol %, from 0.1 vol % to 1.0 vol %, from 0.1 vol % to 0.8 vol %, or from 0.1 vol % to 0.5 vol %. In embodiments, the concentration of oxygen in the oxidative atmosphere that is periodically introduced in the reaction zone is from 0.5 vol % to 3.0 vol %, such as from 1.0 vol % to 2.5 vol %, or from 1.5 vol % to 2.0 vol %. Other gasses introduced to make up the remainder of the oxidative atmosphere are not limited, but in embodiments may be inert gases (like nitrogen), $CO_2$, or steam. It should be understood that other gasses produced by various process reactions may also be present in the oxidative atmosphere in small amounts, although they are not intentionally introduced into the oxidative atmosphere. By introducing oxygen into the reaction zone and at high temperatures, oxidation process can take place at the surface of the components comprising dual-particle hybrid catalyst. Without being bound by any particular theory, it is believed that this oxidative treatment restores some surface properties of the oxide component prepared in the first place by calcination. It is also believed that the treatment removes some typical by-product of the syngas conversion. The net of these effects is to exhibit a high and steady yield of $C_2$ to $C_4$ olefins, even as the catalyst time on stream increases.

The flow rate of the oxidative atmosphere is not particularly limited. In embodiments, the flow rate of the oxidative atmosphere is selected based on practical considerations, such as rates of heat transfer, costs associated with moving gasses into and from the reaction zone, and safety considerations. According to embodiments, there is initially a lower flow of the oxidative atmosphere then higher flow rates and more oxygen feed.

As noted above, the oxidative atmosphere can be periodically introduced into the reaction zone so that the hybrid catalyst is periodically exposed to the oxidative atmosphere. This requires that the oxidative atmosphere is introduced into the reaction zone at least twice during operation. In embodiments, the oxidative atmosphere is introduced into the reaction zone at least three times, at least four times, at least five times, at least six times, at least seven times, or at least eight times during operation. Between the periods where the oxidative atmosphere is introduced into the reaction zone, the oxidative atmosphere is discontinued, and the reaction zone is returned to the conversion conditions and the feed stream is reintroduced. In embodiments, the reaction zone is purged with inert gas before and after the oxidative atmosphere is introduced into the reaction zone to better control the oxidation that occurs when the oxidative atmosphere is present in the reaction zone. The frequency at which the oxidative atmosphere is introduced into the reaction zone is determined based on the rate of degradation of the $C_2$ to $C_4$ olefin selectivity. It should be understood that having too short of a time between introduction of an oxidative atmosphere is inefficient because $C_2$ to $C_4$ olefin production is reduced or even cut off when the oxidative atmosphere is introduced into the reaction zone. Therefore, the frequency at which the oxidative atmosphere is introduced into the reaction zone should not be so high that it interferes with efficient production of $C_2$ to $C_4$ olefins. As described above, exposing the hybrid catalyst to an oxidative atmosphere does not increase the $C_2$ to $C_4$ olefin selectivity beyond the initial selectivity, but can prevent the $C_2$ to $C_4$ olefin selectivity from decreasing, thereby exhibiting a high and steady yield of $C_2$ to $C_4$ olefins, even as the catalyst time on stream increases. The number and duration of treatments where an oxidative atmosphere is introduced into the reaction zone may be based on an economic balance of the cost to restore the yield of $C_2$ to $C_4$ olefins of the hybrid catalyst and the lost productivity due to lower olefin yields. There are a number of ways that processes according to embodiments disclosed and described herein may be used to address these concerns.

One way in which this can be achieved is by monitoring the $C_2$ to $C_4$ olefin selectivity in real time and introducing the oxidative atmosphere when the $C_2$ to $C_4$ olefin selectivity decreases by an economically pre-determined amount.

Alternatively, the $C_2$ to $C_4$ olefin conversion process can be modeled, such as on conventional chemical process modeling software, such as ASPEN, and the $C_2$ to $C_4$ olefin selectivity of this modeled process can be measured. The frequency of introducing the oxidative atmosphere into the reaction zone can then be determined based on this modeled process. As a non-limiting example, if the modeled process indicates that $C_2$ to $C_4$ olefin selectivity decreases after 100 hours on stream, the oxidative atmosphere may be periodically introduced into the reaction zone every 50 hours. As another alternative, a pilot plant or lab scale model of the process may be made and $C_2$ to $C_4$ olefin selectivity may be measure on the pilot plant or lab scale model to determine the frequency of the periods where an oxidative atmosphere is introduced into the reaction zone.

As mentioned above, the frequency of periods where an oxidative atmosphere is introduced into the reaction zone will depend on the loss in $C_2$ to $C_4$ selectivity and the economic balance between this lost productivity and costs of regeneration. In embodiments, the frequency of the periods where an oxidative atmosphere is introduced into a reaction zone is from 20 hours to 1000 hours—meaning that an oxidative atmosphere is introduced into the reaction every 20 hours to every 1000 hours—such as from 50 hours to 1000 hours, from 100 hours to 1000 hours, from 150 hours to 1000 hours, from 200 hours to 1000 hours, from 250 hours to 1000 hours, from 300 hours to 1000 hours, from 350 hours to 1000 hours, from 400 hours to 1000 hours, from 450 hours to 1000 hours, from 500 hours to 1000 hours, from 550 hours to 1000 hours, from 600 hours to 1000 hours, from 650 hours to 1000 hours, from 700 hours to 1000 hours, from 750 hours to 1000 hours, from 800 hours to 1000 hours, from 850 hours to 1000 hours, from 900 hours to 1000 hours, or from 950 hours to 1000 hours. In embodiments, the frequency of the periods where an oxidative atmosphere is introduced into a reaction zone is from 20 hours to 950 hours, such as from 20 hours to 900 hours, from 20 hours to 850 hours, from 20 hours to 800 hours, from 20 hours to 750 hours, from 20 hours to 700 hours, from 20 hours to 650 hours, from 20 hours to 600 hours, from 20 hours to 550 hours, from 20 hours to 500 hours, from 20 hours to 450 hours, from 20 hours to 400 hours, from 20 hours to 350 hours, from 20 hours to 300 hours, from 20 hours to 250 hours, from 20 hours to 200 hours, from 20 hours to 150 hours, from 20 hours to 100 hours, or from 20 hours to 50 hours. In embodiments, the frequency of the periods where an oxidative atmosphere is introduced into a reaction zone is from 20 hours to 300 hours, such as from 40 hours to 300 hours, from 60 hours to 300 hours, from 80 hours to 300 hours, from 100 hours to 300 hours, from 120 hours to 300 hours, from 140 hours to 300 hours, from 160 hours to 300 hours, from 180 hours to 300 hours, from 200 hours to 300 hours, from 220 hours to 300 hours, from 240 hours to 300 hours, from 260 hours to 300 hours, or from 280 hours to 300 hours. In embodiments, the frequency of the periods where an oxidative atmosphere is introduced into a reaction zone is from 20 hours to 280 hours, such as from 20 hours to 260 hours, from 20 hours to 240 hours, from 20 hours to 220 hours, from 20 hours to 200 hours, from 20 hours to 180 hours, from 20 hours to 160 hours, from 20 hours to 140 hours, from 20 hours to 120 hours, from 20 hours to 100 hours, from 20 hours to 80 hours, from 20 hours to 60 hours, or from 20 hours to 60 hours. In embodiments, the frequency of the periods where an oxidative atmosphere is introduced into a reaction zone is from 40 hours to 280 hours, from 60 hours to 260 hours, from 80 hours to 240 hours, from 100 hours to 220 hours, from 120 hours to 200 hours, or from 140 hours to 180 hours.

In embodiments, the feed stream comprising $H_2$ gas and a carbon-containing gas selected from $CO$, $CO_2$, and combinations thereof is not introduced into the reaction zone while the oxidative atmosphere is introduced into the reaction zone. Accordingly, in one or more embodiments, only one of the feed stream or the oxidative atmosphere is introduced into the reaction zone at any given point in time. In embodiments, the feed stream is discontinued and an oxidative atmosphere is introduced into the reaction zone for a set duration. In embodiments, the oxidative atmosphere will be introduced into the reaction zone until the $O_2$ concentration of the outgoing stream matches the $O_2$ concentration of the incoming oxidative atmosphere. In embodiments, the duration for which the oxidative atmosphere is introduced into the reaction zone is from 5 hours to 30 hours, such as from 8 hours to 30 hours, from 10 hours to 30 hours, from 12 hours to 30 hours, from 15 hours to 30 hours, from 18 hours to 30 hours, from 20 hours to 30 hours, from 22 hours to 30 hours, from 25 hours to 30 hours, or from 28 hours to 30 hours. In embodiments, the duration is from 5 hours to 28 hours, such as from 5 hours to 25 hours, from 5 hours to 22 hours, from 5 hours to 20 hours, from 5 hours to 18 hours, from 5 hours to 15 hours, from 5 hours to 12 hours, from 5 hours to 10 hours, or from 5 hours to 8 hours. In embodiments, the duration is from 8 hours to 28 hours, such as from 10 hours to 25 hours, from 12 hours to 22 hours, from 15 hours to 20 hours, or about 18 hours.

As described above, when the oxidative atmosphere is added to the reaction zone the feed stream is, in embodiments, discontinued. Accordingly, the conversion conditions (such as, for example, temperature and pressure) may, in embodiments, also be discontinued and the temperature and pressure within the reaction zone may be adjusted to promote the oxidation. In embodiments, during a period where an oxidative atmosphere is introduced into the reaction zone, the temperature in the reaction zone may be from ambient temperature (such as room temperature or about 20° C.) to 700° C., such as from 50° C. to 700° C., from 100° C. to 700° C., from 150° C. to 700° C., from 200° C. to 700° C., from 250° C. to 700° C., from 300° C. to 700° C., from 350° C. to 700° C., from 400° C. to 700° C., from 450° C. to 700° C., from 500° C. to 700° C., from 550° C. to 700° C., from 600° C. to 700° C., or from 650° C. to 700° C. In embodiments, during a period where an oxidative atmosphere is introduced into the reaction zone, the temperature in the reaction zone may be from ambient temperature to 700° C., such as from ambient temperature to 650° C., from ambient temperature to 600° C., from ambient temperature to 550° C., from ambient temperature to 500° C., from ambient temperature to 450° C., from ambient temperature to 400° C., from ambient temperature to 350° C., from ambient temperature to 300° C., from ambient temperature to 250° C., from ambient temperature to 200° C., from ambient temperature to 150° C., from ambient temperature to 100° C., or from ambient temperature to 50° C. In one or more embodiments, during a period where an oxidative atmosphere is introduced into the reaction zone, the temperature in the reaction zone may be from 420° C. to 550° C., such as from 430° C. to 540° C., from 440° C. to 530° C., from 450° C. to 520° C., from 460° C. to 510° C., from 470° C. to 500° C., or from 480° C. to 490° C. Accordingly, in some embodiments, the temperature of the reaction zone during a period where an oxidative atmosphere is introduced into the reaction zone may be the same, or about the same as, the temperature of the conversion conditions, but in other embodiments, the temperature of the reaction zone during a period where an oxidative atmosphere is introduced into the reaction zone may be different than the temperature of the conversion conditions.

In embodiments, during a period where an oxidative atmosphere is introduced into the reaction zone, the pressure in the reaction zone may be from 1 bar (100 kPa) to 100 bar (5,000 kPa), such as from 5 bar (500 kPa) to 100 bar (10,000 kPa), from 10 bar (1,000 kPa) to 100 bar (10,000 kPa), from 20 bar (2,000 kPa) to 100 bar (10,000 kPa), from 30 bar (3,000 kPa) to 100 bar (10,000 kPa), from 40 bar (4,000 kPa) to 100 bar (10,000 kPa), from 50 bar (5,000 kPa) to 100 bar (10,000 kPa), from 60 bar (6,000 kPa) to 100 bar (10,000 kPa), from 70 bar (7,000 kPa) to 100 bar (10,000 kPa), from 80 bar (8,000 kPa) to 100 bar (10,000 kPa), or from 90 bar (9,000 kPa) to 100 bar (10,000 kPa). In embodiments, during a period where an oxidative atmosphere is introduced into the reaction zone, the pressure in the reaction zone may be from 1 bar (100 kPa) to 90 bar (9,000 kPa), from 1 bar (100 kPa) to 80 bar (8,000 kPa), from 1 bar (100 kPa) to 70 bar (7,000 kPa), from 1 bar (100 kPa) to 60 bar (6,000 kPa), from 1 bar (100 kPa) to 50 bar (5,000 kPa), from 1 bar (100 kPa) to 40 bar (4,000 kPa), from 1 bar (100 kPa) to 30 bar (3,000 kPa), from 1 bar (100 kPa) to 20 bar (2,000 kPa), or from 1 bar (100 kPa) to 10 bar (1,000 kPa). In embodiments, during a period where an oxidative atmosphere is introduced into the reaction zone, the pressure in the reaction zone may be from 1 bar (100 kPa) to 60 bar (6,000 kPa), such as from 5 bar (500 kPa) to 60 bar (6,000 kPa), from 10 bar (1,000 kPa) to 60 bar (6,000 kPa), from 15 bar (1,500 kPa) to 60 bar (6,000 kPa), from 20 bar (2,000 kPa) to 60 bar (6,000 kPa), from 25 bar (2,500 kPa) to 60 bar (6,000 kPa), from 30 bar (3,000 kPa) to 60 bar (6,000 kPa), from 35 bar (3,500 kPa) to 60 bar (6,000 kPa), from 40 bar (4,000 kPa) to 60 bar (6,000 kPa), from 45 bar (4,500 kPa) to 60 bar (6,000 kPa), from 50 bar (5,000 kPa) to 60 bar (6,000 kPa), or from 55 bar (5,500 kPa) to 60 bar (6,000 kPa). In embodiments, during a period where an oxidative atmosphere is introduced into the reaction zone, the pressure in the reaction zone may be from 1 bar (100 kPa) to 55 bar (5,500 kPa), from 1 bar (100 kPa) to 50 bar (5,000 kPa), form 1 bar (100 kPa) to 45 bar (4,500 kPa), from 1 bar (100 kPa) to 40 bar (4,000 kPa), from 1 bar (100 kPa) to 35 bar (3,500 kPa), from 1 bar (100 kPa) to 30 bar (3,000 kPa), from 1 bar (100 kPa) to 25 bar (2,500 kPa), from 1 bar (100 kPa) to 20 bar (2,000 kPa), from 1 bar (100 kPa) to 15 bar (1,500 kPa), from 1 bar (100 kPa) to 10 bar (1,000 kPa), or from 1 bar (100 kPa) to 5 bar (500 kPa). Accordingly, in some embodiments, the pressure of the reaction zone during a period where an oxidative atmosphere is introduced into the reaction zone may be the same, or about the same as, the pressure of the conversion conditions, but in other embodiments, the pressure of the reaction zone during a period where an oxidative atmosphere is introduced into the reaction zone may be different than the pressure of the conversion conditions.

By using processes disclosed and described herein, the $C_2$ to $C_4$ olefin selectivity exhibits a high and steady yield of $C_2$ to $C_4$ olefins, even as the catalyst time on stream increases. One way of measuring the effective loss of the $C_2$ to $C_4$ olefin selectivity is by comparing the $C_2$ to $C_4$ olefin selectivity at a relatively short time on stream to the $C_2$ to $C_4$ olefin selectivity after the hybrid catalyst has been on stream for a significant amount of time. For example, the $C_2$ to $C_4$ olefin selectivity may be measured after the hybrid catalyst has been on stream for 50 hours and compared to the $C_2$ to $C_4$ olefin selectivity after the hybrid catalyst has been on stream for 500 hours. As a non-limiting example, if the $C_2$ to $C_4$ olefin selectivity is 35 Cmol % after the hybrid catalyst has been on stream for 50 hours and the $C_2$ to $C_4$ olefin selectivity is 33 Cmol % after the hybrid catalyst has been on stream for 500 hours, the loss of the $C_2$ to $C_4$ olefin selectivity can be expressed as the absolute difference between these two values (i.e., 2 Cmol %).

According to embodiments, the loss of the $C_2$ to $C_4$ olefin selectivity measured after the hybrid catalyst has been on stream for 50 hours and measured after the hybrid catalyst has been on stream for 500 hours may be less than 15 Cmol %, such as less than 14 Cmol %, less than 13 Cmol %, less than 12 Cmol %, less than 11 Cmol %, less than 10 Cmol %, less than 9 Cmol %, less than 8 Cmol %, less than 7 Cmol %, less than 6 Cmol %, less than 5 Cmol %, less than 4 Cmol %, less than 3 Cmol %, or less than 2 Cmol %. In embodiments, the loss of the $C_2$ to $C_4$ olefin selectivity measured after the hybrid catalyst has been on stream for 50 hours and measured after the hybrid catalyst has been on stream for 500 hours may be from 2 Cmol % to 15 Cmol %, such as from 2 Cmol % to 14 Cmol %, from 2 Cmol % to 13 Cmol %, from 2 Cmol % to 12 Cmol %, from 2 Cmol % to 11 Cmol %, from 2 Cmol % to 10 Cmol %, from 2 Cmol % to 9 Cmol %, from 2 Cmol % to 8 Cmol %, from 2 Cmol % to 7 Cmol %, from 2 Cmol % to 6 Cmol %, from 2 Cmol % to 5 Cmol %, or from 2 Cmol % to 4 Cmol %.

EXAMPLES

Catalyst Preparation

A supported metal oxide catalyst component of Ga—La/$ZrO_2$ was prepared by an incipient wetness impregnation method. Stock solutions of gallium (III) nitrate hydrate with C=2 M in de-ionize (DI) water and lanthanum (III) nitrate hydrate with C=0.75 M in DI water were prepared. Then, 1000 μl of the Gallium stock solution was mixed with 800 μl of Lanthanum solution and 200 μl of DI water to obtain 2000 μl of the impregnation solution. Subsequently, 5 g of 40-80 mesh size $ZrO_2$ support (NORPRO, SZ31164, BET surface area=98 $m^2$/g, 100% monoclinic phase (measured by XRD), pore volume=0.4 ml/g (measured by DI water)) was weighed and placed into a glass vial. After that, 2000 μl of the impregnation solution was added dropwise to the support and providing sufficient mixing to ensure homogeneous impregnation. After impregnation, the catalyst was dried at 85° C. in an oven (static air) overnight and calcined at 550° C. for 4 hours using a heating rate of 3° C./min. After calcination, the catalyst was re-sieved to 60-80 mesh size to remove fine particles.

The reactor effluent composition was obtained by gas chromatography and the conversion and selectivities were calculated using the following equations:

CO Conversion=$X_{CO}(\%)=[(n_{CO,in}-n_{CO,out})/n_{CO,in}]\cdot 100$, where $n_{CO}$ is the molar flow[mol/1] of CO; and Selectivity of product $j$=$S_j(\%)=[a_j \cdot n_{j,out}/(n_{CO,in}-n_{CO,out})]\cdot 100$, where a is the number of carbon atoms for product $j$,$n_{j,out}$ is the molar outlet of product $j$.

Example 1

A process according to embodiments was performed and will be described with reference to FIGS. 1A to 1D. The hybrid catalyst was 80 vol % $Ga/ZrO_2$ sized particles and 20 vol % SAPO-34 sized particles made as disclosed above. The amounts of the sized 60-80 mesh mixed oxide particles used to prepare hybrid catalyst beds are reported in the Table below. Hybrid catalysts were prepared upon gentle shaking of particles together in a vial.

TABLE 1

| Metal Oxide Component Vol. ($cm^3$) Mean | Microporous Component Vol. ($cm^3$) Mean | Catalyst Bed Vol. ($cm^3$) Mean | Metal Oxide Vol. Fraction Mean | Nominal GHSV ($h^{-1}$) Mean |
|---|---|---|---|---|
| 0.192 | 0.047 | 0.237 | 0.8 | 3797.5 |
| 0.189 | 0.049 | 0.237 | 0.8 | 3797.5 |
| 0.190 | 0.049 | 0.237 | 0.8 | 3797.5 |

The conversion conditions (indicated as C1 to C7 in FIG. 1A) were as follows: temperature of 420° C.; pressure of 40 bar (4,000 kPa); and a feed $H_2/CO$ ratio of about 3. The feed of syngas was distributed in an equal amount of 15 sccm per tube that in correspondence to the total volume of the hybrid catalyst bed resulted in GHSV of 3800 $h^{-1}$.

Figure 1A:
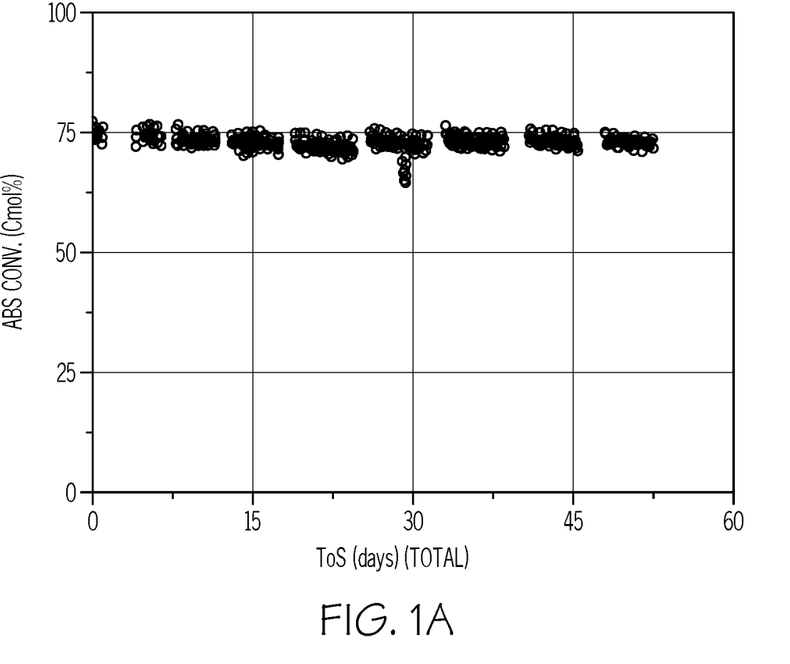
FIG. 1A is a graph showing carbon conversion versus time on stream for a process according to embodiments disclosed and described herein.
Figure 1B:
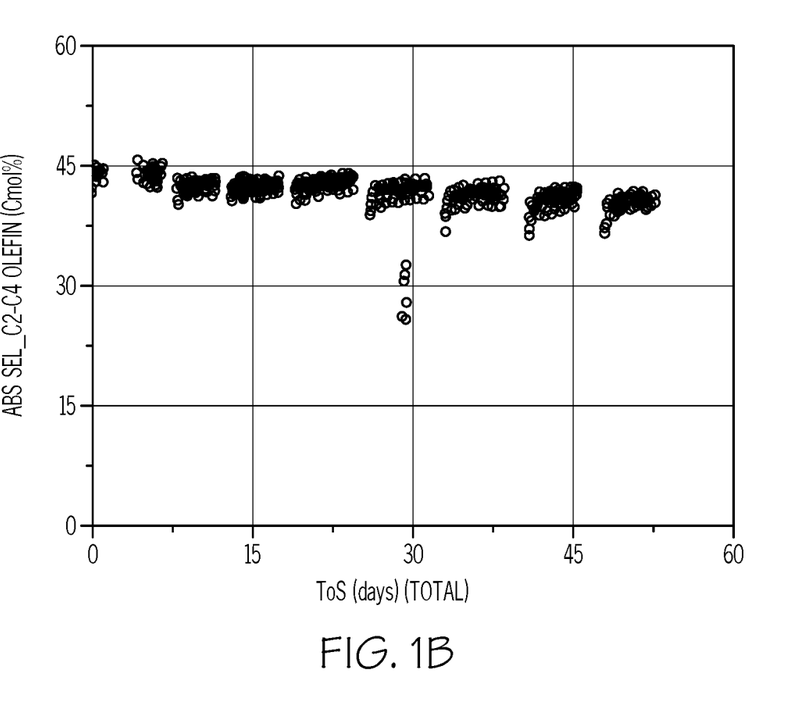
FIG. 1B is a graph showing $C_2$ to $C_4$ olefin selectivity versus time on stream for a process according to embodiments disclosed and described herein.
Figure 1C:
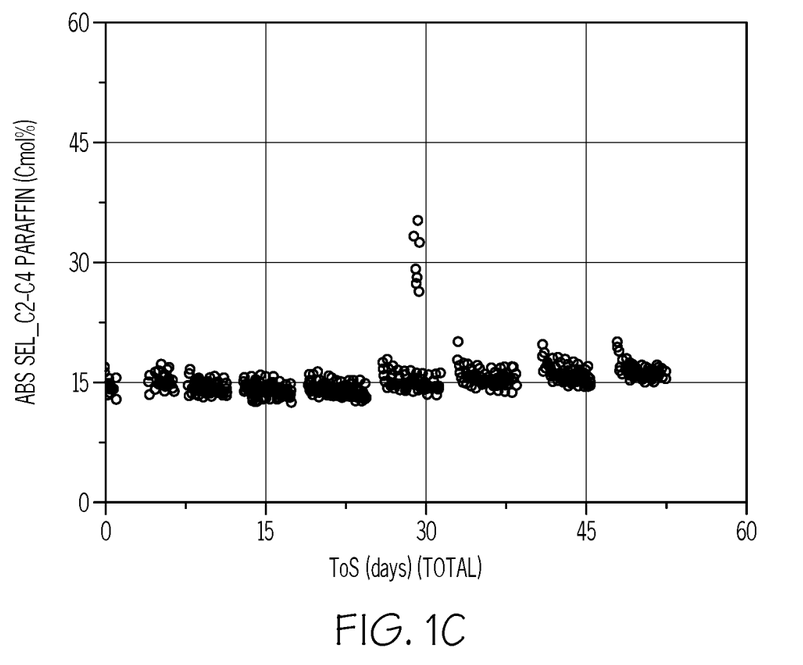
FIG. 1C is a graph showing $C_2$ to $C_4$ paraffin selectivity versus time on stream for a process according to embodiments disclosed and described herein.

The trends in (i) conversion of carbon monoxide and (ii) in selectivity to $C_2$-$C_4$ olefins over each of replicates developing in process time are presented in FIGS. 1A and 1B.

The table below summarizes mean values in conversion of carbon monoxide, in $C_2$-$C_4$ olefin product selectivity, in methane by-product selectivity and in carbon dioxide selectivity formed during this process.

| Condition | Conversion (Cmol %) Mean | $C_2$ to $C_4$ Olefin Selectivity (Cmol %) Mean | Methane Selectivity (Cmol %) Mean | $CO_2$ Selectivity (Cmol %) Mean |
|---|---|---|---|---|
| C1 | 73.9 | 44.0 | 1.0 | 34.3 |
| C2 | 73.2 | 42.4 | 1.1 | 33.9 |
| C3 | 27.7 | 42.3 | 1.1 | 33.9 |
| C4 | 71.9 | 42.7 | 1.2 | 34.6 |
| C5 | 72.1 | 41.0 | 1.1 | 34.2 |
| C6 | 72.9 | 41.3 | 1.1 | 34.0 |
| C7 | 73.0 | 40.3 | 1.4 | 33.9 |
| C8 | 72.8 | 40.3 | 1.3 | 33.8 |

Between these conversion conditions, an oxidative atmosphere was periodically introduced into the reaction zone as shown in FIG. 1A. In particular, an oxidative atmosphere was introduced into the reaction zone when the selectivity of $C_2$ to $C_4$ olefins started to drop, this resulted in an oxidative atmosphere being introduced into the reaction zone at about 200 hours on stream (R1 in FIG. 1A), about 300 hours on stream (R2 in FIG. 1A), about 450 hours on stream (R3 in FIG. 1A), about 600 hours on stream (R4 in FIG. 1A), about 775 hours on stream (R5 in FIG. 1A), about 950 hours on stream (R6 in FIG. 1A), and about 1100 hours on stream (R7 in FIG. 1A). The conditions of the oxidative atmospheres that were used (indicated as R1 to R7 in FIG. 1A) are provided in Table 1 below:

TABLE 1

| R | Type | $O_2$ vol % | T [° C.] | Duration [h] |
|---|---|---|---|---|
| 1 | [O] | 1 | 420 | 18 |
| 2 | [O] | 1 | 420 | 18 |
| 3 | [O] | 2 | 420 | 18 |
| 4 | [O] | 1-3 | 420 | 18 |

TABLE 1-continued

| R | Type | $O_2$ vol % | T [° C.] | Duration [h] |
|---|---|---|---|---|
| 5 | [O] | 1-3 | 540 | 18 |
| 6 | 1) [O] | 1-3 | 540 | 18 for [O] |
|   | 2) [H] |  | 420 | 24 or [H] |
| 7 | 1) In situ [O] | 1-3 | 540 | 18 for [O] in situ |
|   | 2) Ex situ [O] | air | 600 | 4 for [O] ex situ |

In Table 1, [O] indicates an oxidative condition using the oxygen content as indicated in the Table 1 where the balance was one or more inert gases. For R6, the oxidative treatment was followed by a reductive treatment in hydrogen (indicated as [H] in Table 1). For R7, the catalyst was taken out of the reaction zone after an in situ oxidative treatment and then further treated in air ex situ before being returned to the reaction zone.

As noted above, the results of these tests are shown in FIGS. 1A to 1D. As shown in these figures, the carbon conversion was above 60% even after the hybrid catalyst has been on stream for 1000 hours, the $C_2$ to $C_4$ olefin selectivity was around 40 Cmol % after the hybrid catalyst had been on stream for about 50 hours and was above 35 Cmol % even after the hybrid catalyst had been on stream for about 1200 hours, the $C_2$ to $C_4$ paraffin selectivity increased slightly from around 13 Cmol % after the hybrid catalyst had been on stream for about 50 hours and was below 20 Cmol % even after the hybrid catalyst had been on stream for about 1200 hours, and the methane selectivity remained below 2 Cmol % even after the hybrid catalyst had been on stream for about 1200 hours.

Figure 1D:
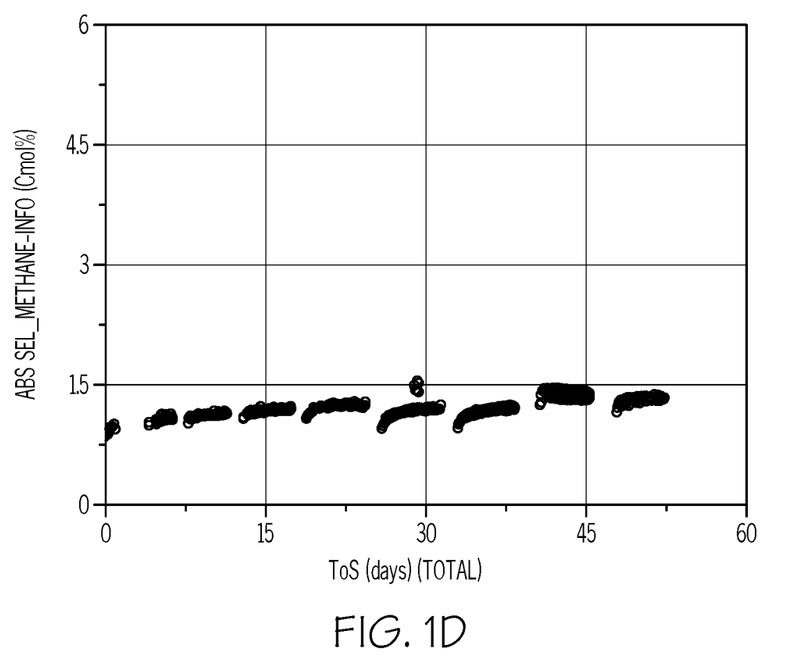
FIG. 1D is a graph showing methane selectivity versus time on stream for a process according to embodiments disclosed and described herein.
Figure 2A:
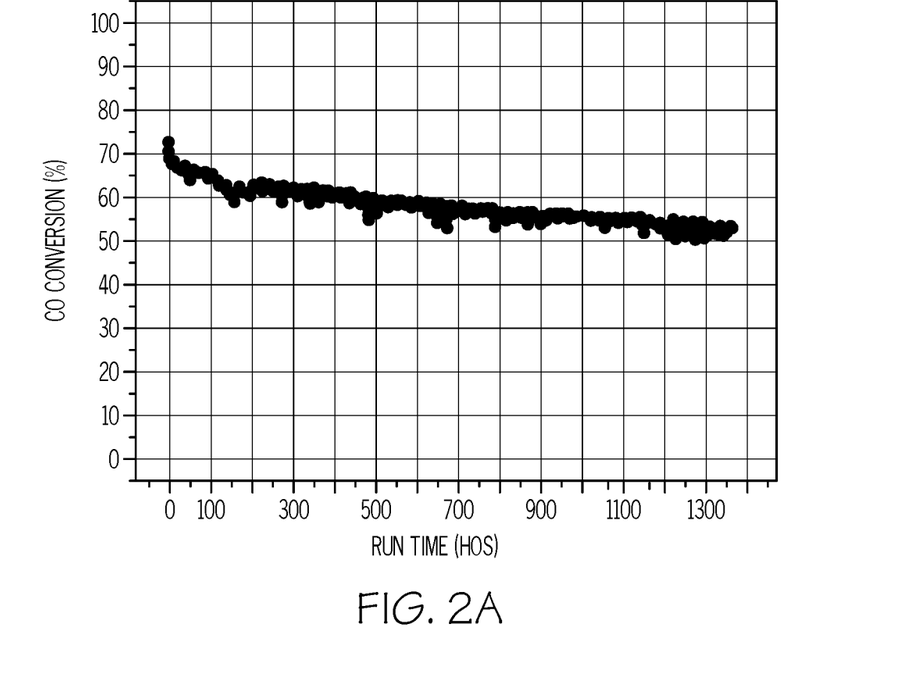
FIG. 2A is a graph showing carbon conversion versus time on stream for a carbon conversion process.
Figure 2B:
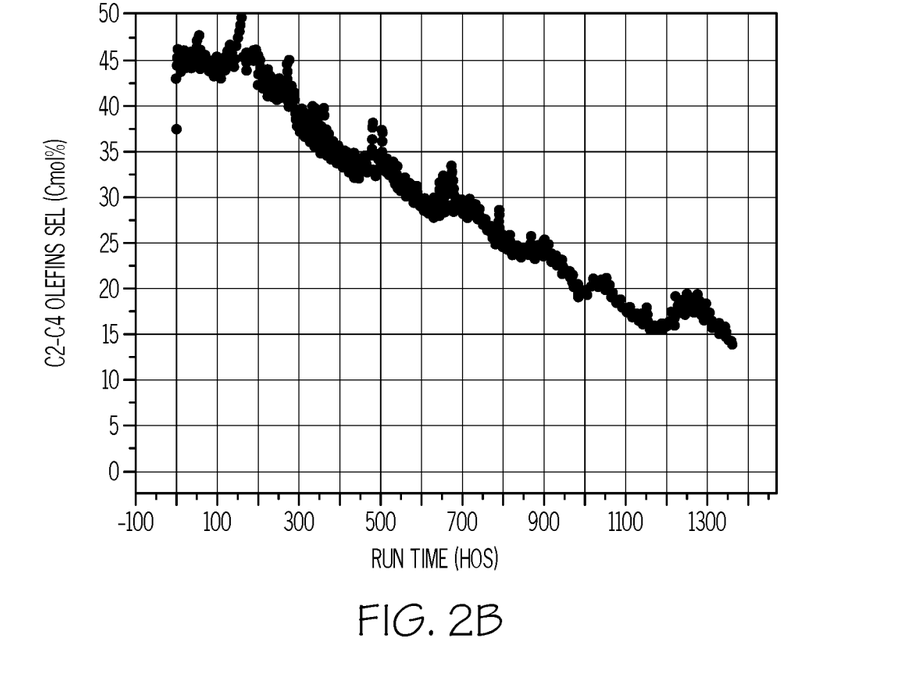
FIG. 2B is a graph showing $C_2$ to $C_3$ olefin selectivity versus time on stream for a carbon conversion process.
Figure 2C:
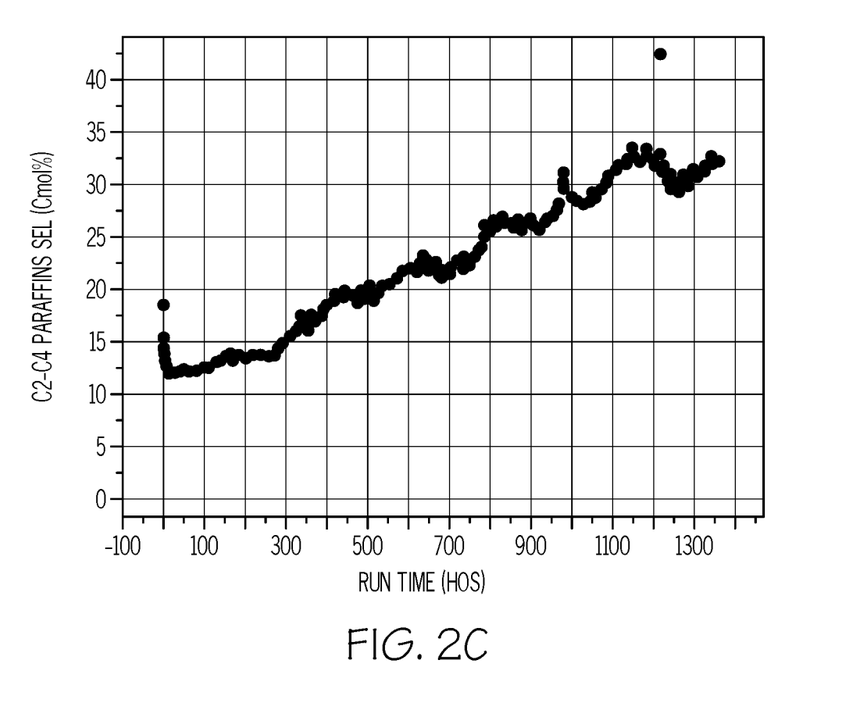
FIG. 2C is a graph showing $C_2$ to $C_3$ paraffin selectivity versus time on stream for a carbon conversion process.
Figure 2D:
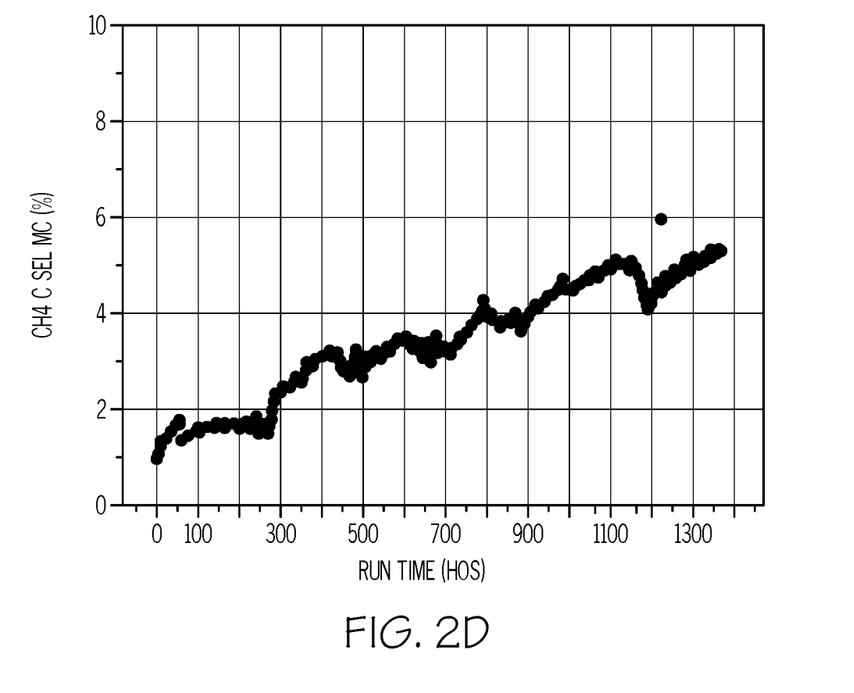
FIG. 2D is a graph showing methane selectivity versus time on stream for a carbon conversion process.

Example 1 demonstrates the stable performance engendered by the periodic treatments according to embodiments disclosed and described herein and as set forth in Table 1. Over 1000 hours of operation, CO conversion and $C_2$ to $C_4$ olefin selectivity only drop by about 5% [Cmol %] (as shown in FIGS. 1A and 1B). Additionally, the increase in methane selectivity is more muted than the comparative examples as shown in FIG. 1D.

Comparative Example 1

This comparative example shows the instability of continuous operations under conventional conversion conditions. The hybrid catalyst was the same as used in Example 1. The conversion conditions were as follows: temperature of 430° C.; pressure of 50 bar (5,000 kPa); GHSV of 5500 $h^{-1}$, and a feed $H_2/CO$ ratio of about 3.

The results of these tests are shown in FIGS. 2A to 2D. As shown in these figures, the carbon conversion dropped from about 70% when the hybrid catalyst was on stream for about 50 hours to about 50% after the hybrid catalyst has been on stream for 1000 hours, the $C_2$ to $C_4$ olefin selectivity was around 45 Cmol % after the hybrid catalyst had been on stream for about 50 hours and was around 15 Cmol % after the hybrid catalyst had been on stream for about 1200 hours, the $C_2$ to $C_4$ paraffin selectivity increased from around 12 Cmol % after the hybrid catalyst had been on stream for about 50 hours and to about 30 Cmol % after the hybrid catalyst had been on stream for about 1200 hours, and the methane selectivity increased from about 2 Cmol % after the hybrid catalyst had been on stream for about 50 hours to about 5 Cmol % after the hybrid catalyst had been on stream for about 1150 hours.

This comparative example demonstrates the overall instability of continuous operation under these conditions. Specifically, target $C_2$ to $C_4$ olefin selectivity drops by over 30

Cmol % over about 1000 hours of operation. This coincides with a 3-fold increase in paraffin selectivity and an almost 6-fold increase in methane selectivity. Additionally, CO conversion decreases by about 10% over this timeframe.

Comparative Example 2

This comparative example shows the instability of continuous operations under conventional conversion conditions. The hybrid catalyst was 60 vol % Ga/ZrO$_2$ and 40 vol % SAPO-34, prepared as disclosed above. The conversion conditions were as follows: temperature of 420° C.; pressure of 40 bar (4,000 kPa); GHSV of 3600 h$^{-1}$, and a feed H$_2$/CO ratio of about 3.

Figure 3A:
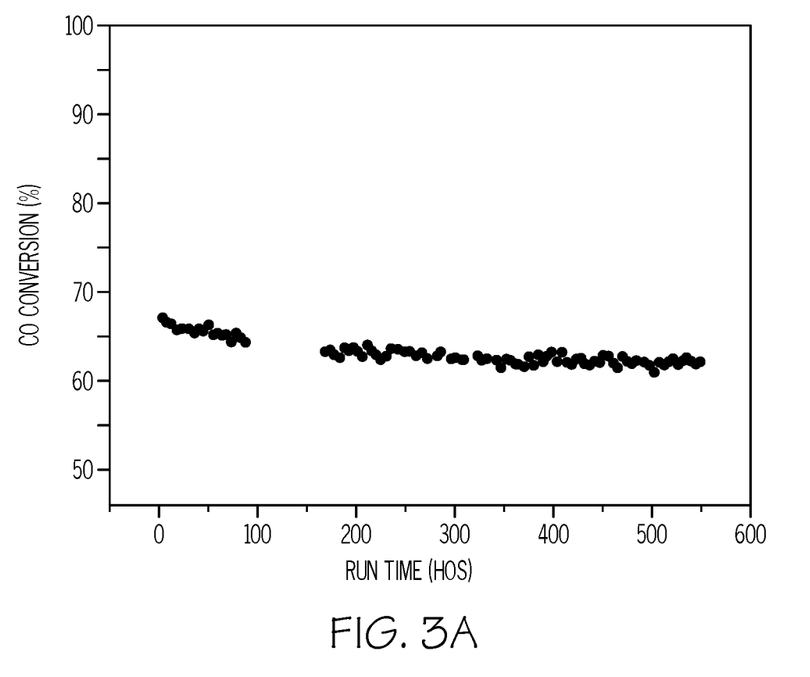
FIG. 3A is a graph showing carbon conversion versus time on stream for a carbon conversion process.
Figure 3B:
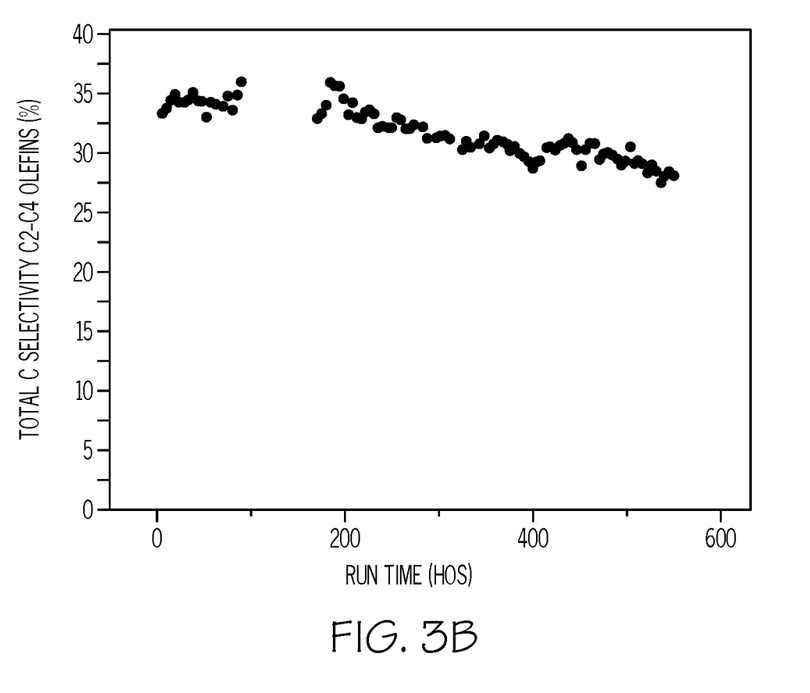
FIG. 3B is a graph showing $C_2$ to $C_4$ olefin selectivity versus time on stream for a carbon conversion process.
Figure 3C:
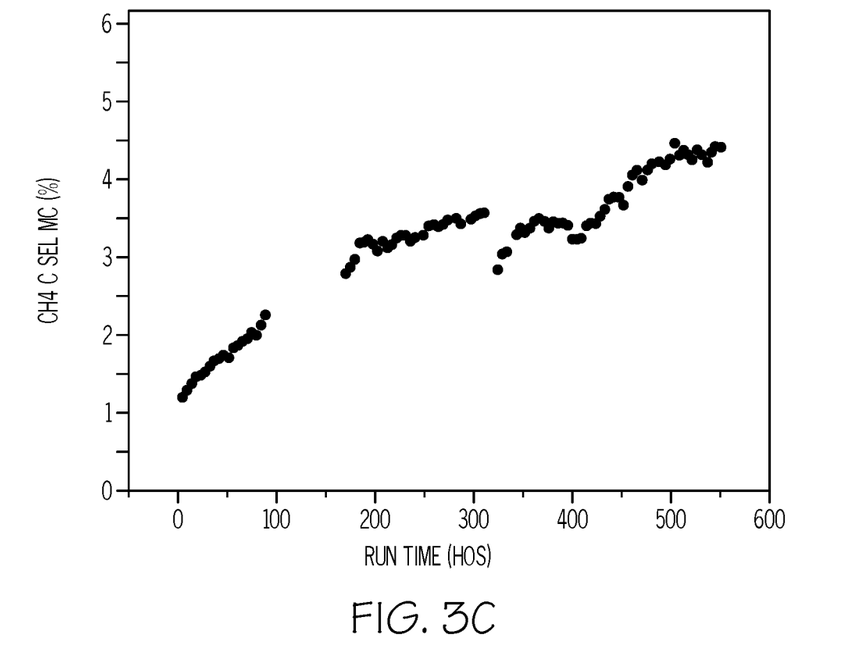
FIG. 3C is a graph showing methane selectivity versus time on stream for a carbon conversion process.

The results of these tests are shown in FIGS. 3A to 3C. As shown in these figures, the carbon conversion dropped from about 70% when the hybrid catalyst was on stream for about 50 hours to about 60% after the hybrid catalyst has been on stream for 500 hours, the C$_2$ to C$_4$ olefin selectivity was around 35 Cmol % after the hybrid catalyst had been on stream for about 50 hours and was around 27 Cmol % after the hybrid catalyst had been on stream for about 500 hours, and the methane selectivity increased from about 1 Cmol % after the hybrid catalyst had been on stream for about 50 hours to about 4.5 Cmol % after the hybrid catalyst had been on stream for about 500 hours.

This comparative example demonstrates the overall instability of continuous operation under conditions comparable to Example 1. Specifically, target C$_2$ to C$_4$ olefin selectivity drops by over 5 Cmol % over about 550 hours of operation. Extrapolating to the run time of Example 1, this would lead to a loss in olefin selectivity of greater than 10 Cmol %. This coincides with a 4-fold increase in in methane selectivity, and a decrease in CO conversion decreases by less than 10% over this timeframe.

It will be apparent to those skilled in the art that various modifications and variations can be made to the embodiments described herein without departing from the spirit and scope of the claimed subject matter. Thus, it is intended that the specification cover the modifications and variations of the various embodiments described herein provided such modification and variations come within the scope of the appended claims and their equivalents.

The invention claimed is:

1. A process for preparing C$_2$ to C$_4$ olefins comprising:
   introducing a feed stream comprising hydrogen gas and a carbon-containing gas selected from the group consisting of carbon monoxide, carbon dioxide, and mixtures thereof into a reaction zone of a reactor;
   converting the feed stream into a product stream comprising C$_2$ to C$_4$ olefins in the reaction zone in the presence of a hybrid catalyst and in a non-oxidative atmosphere, the hybrid catalyst comprising:
   a metal oxide catalyst component comprising gallium oxide and zirconia; and
   a microporous catalyst component comprising an 8 membered ring pore opening; and
   periodically introducing an oxidative atmosphere into the reaction zone.

2. The process of claim 1, wherein the oxidative atmosphere comprises from 0.1 vol % to 99.9 vol % oxygen.

3. The process of claim 1, wherein the oxidative atmosphere comprises from 0.5 vol % to 3.0 vol % oxygen.

4. The process of claim 1, wherein the balance of the oxidative atmosphere is inert gases.

5. The process of claim 1, wherein the non-oxidative atmosphere comprises less than 0.1 vol % oxygen.

6. The process of claim 1, wherein a frequency of periods where an oxidative atmosphere is introduced into a reaction zone is from 20 hours to 1000 hours.

7. The process of claim 1, wherein a duration for which the oxidative atmosphere is introduced into the reaction zone is from 5 hours to 30 hours.

8. The process of claim 1, wherein the microporous catalyst component comprises SAPO-34.

9. The process of claim 1, wherein the metal oxide catalyst component comprises from 60.0 wt % to 90.0 wt % of the hybrid catalyst.

10. The process of claim 1, wherein a temperature within the reaction zone while introducing the oxidative atmosphere is from ambient to 700° C.

11. The process of claim 1, wherein a temperature within the reaction zone while introducing the oxidative atmosphere is from 300° C. to 550° C.

12. The process of claim 1, wherein a pressure within the reaction zone while introducing the oxidative atmosphere is from 1 bar (100 kPa) to 50 bar (5,000 kPa).

13. The process of claim 1, wherein a pressure within the reaction zone while introducing the oxidative atmosphere is from 10 bar (3,000 kPa) to 20 bar (4,000 kPa).

14. The process of claim 1, wherein conversion conditions when the feed stream is introduced into the reaction zone comprise:
   a temperature from 350° C. to 450° C.;
   a pressure from 1 bar (100 kPa) to 70 bar (7,000 kPa); and
   a gas hour space velocity (GHSV) from 1200 h$^{-1}$ to 12000 h$^{-1}$.

15. The process of claim 1, wherein loss of a C$_2$ to C$_4$ olefin selectivity measured after the hybrid catalyst has been on stream for 50 hours and measured after the hybrid catalyst has been on stream for 500 hours is less than 15 Cmol %.

16. The process of claim 1, wherein
   the oxidative atmosphere comprises from 0.5 vol % to 3.0 vol % oxygen,
   a temperature within the reaction zone while introducing the oxidative atmosphere is from 300° C. to 550° C., and
   a pressure within the reaction zone while introducing the oxidative atmosphere is from 10 bar (3,000 kPa) to 20 bar (4,000 kPa).

17. The process of claim 1, wherein
   the microporous catalyst component comprises SAPO-34, and
   the metal oxide catalyst component comprises from 60.0 wt % to 90.0 wt % of the hybrid catalyst.

18. The process of claim 16, wherein
   the microporous catalyst component comprises SAPO-34, and
   the metal oxide catalyst component comprises from 60.0 wt % to 90.0 wt % of the hybrid catalyst.

* * * * *